(12) United States Patent
Tocque

(10) Patent No.: US 7,884,082 B2
(45) Date of Patent: *Feb. 8, 2011

(54) COMBINED THERAPEUTICAL TREATMENT OF HYPERPROLIFERATIVE DISEASES

(75) Inventor: Bruno Tocque, Courbevoie (FR)

(73) Assignee: Aventis Pharma SA, Antony (FR)

( * ) Notice: Subject to any disclaimer, the term of this patent is extended or adjusted under 35 U.S.C. 154(b) by 739 days.

This patent is subject to a terminal disclaimer.

(21) Appl. No.: 10/412,684

(22) Filed: Apr. 14, 2003

(65) Prior Publication Data

US 2004/0127437 A1 Jul. 1, 2004
US 2005/0209177 A9 Sep. 22, 2005

Related U.S. Application Data

(63) Continuation of application No. 09/816,144, filed on Mar. 26, 2001, now abandoned, which is a continuation of application No. 08/875,222, filed as application No. PCT/FR96/00056 on Jan. 12, 1996, now Pat. No. 6,262,032.

(30) Foreign Application Priority Data

Jan. 17, 1995 (FR) .................................. 95 00436

(51) Int. Cl.
*A61K 48/00* (2006.01)
*C12N 15/74* (2006.01)

(52) U.S. Cl. .................................. 514/44 R; 435/320.1
(58) Field of Classification Search ............... 514/44 R; 435/320.1
See application file for complete search history.

(56) References Cited

U.S. PATENT DOCUMENTS

| 5,747,469 | A | * | 5/1998 | Roth et al. ..................... 514/44 |
| 5,932,210 | A | | 8/1999 | Gregory et al. |
| 6,054,467 | A | | 4/2000 | Gjerset |
| 6,069,134 | A | | 5/2000 | Roth et al. |
| 6,165,779 | A | | 12/2000 | Engler et al. |
| 6,262,032 | B1 | * | 7/2001 | Tocque ......................... 514/44 |
| 6,805,858 | B1 | | 10/2004 | Zhang et al. |

FOREIGN PATENT DOCUMENTS

WO WO 87/05943 10/1987

OTHER PUBLICATIONS

Vogelstein et al. (1993) Trends in Genetics, vol. 9(4), 138-141.*
Ledley, (1991) Human Gene Therapy, vol. 2, 77-83.*
Verma et al. (1997) Nature, vol. 389, 239-242.*
Orkin et al. (1995) "Report and recommendations of the panel to assess the NIH investment in research on gene therapy".*
Rainov et al. (2001) Curr. Gene Ther., vol. 1, 367-383.*
W. James (1991), Antiviral Chemistry & Chemotherapy, vol. 2(4), 191-214.
Fisher, et al. (1994), Blood, vol. 84 (10 supl.), 111a.
Verma, et al. (1997), Nature, vol. 389, 239-242.
F.D. Ledley (1991), Human Gene Therapy, vol. 2, 77-83.
Mituzani, et al. (1994), Cancer, vol. 74, 2546-54.
Vogelstein, et al. (1993), Trends in Genetics, vol. 9 (4), 138-141.
Orkin, et al. (1995), "Report and Recommendations of the Panel to Assess the NIH Investment in Research on Gene Therapy."
Fijiwara, et al. (1994), Cancer Research, vol. 54, 2287-2291.
L.L. Nielsen, et al., "Adenovirus-mediated p53 Gene Therapy and Paclitaxel Have Synergistic Efficacy in Models of Human Head and Neck, Ovarian, Prostate and Breast Cancer," Clinical Cancer Research, (1988), vol. 4, 835-846.
"NCI Fact Sheet: Paclitaxel (Taxol) and Related Anticancer Drugs—Updated Feb. 2000," OncoLink: NCI Fact Sheet; http://oncolink.upenn.edu/pdq_html/6/engl/600715.html.
Pharmacology of Paclitaxel and Docetaxel [Chemical Comparison Table], 1995 Physician's Desk Reference, Montvale, NJ, Medical Economics Data Production Company; http://biotech.icmb.utexas.edu/botany/tax/html.
R. Lim, et al., "Overexpression of Glia Maturation Factor in C6 Cells Promotes Differentiation and Activates Superoxide Dismutase," Neurochem Res., vol. 23(11), 1998, 1445-51. Abstract Only.
D. Lu, et al., "Regulatable Production of Insulin From Primary-cultured Hepatocytes: Insulin Production is Up-regulated by Glucagen and cAMP and Down-regulated by Insulin," Gene Therapy, vol. 5(7), 1998, 888-95. Abstract Only.
Nielsen, Loretta, L.,et al., "Adenovirus-mediated p53 Gene Therapy and Paclitaxel Have Synergistic Efficacy in Models of Human Head and Neck, Ovarian, Prostate, and Breast Cancer", Clinical Cancer Research, vol. 4, 835-846, Apr. 1998.
Kigawa, J. et al., "p53 gene status and chemosensitivity in ovarian cancer", Human Cell, Sep. 2001; vol. 14(3) pp. 165-171. (Abstract Only).

(Continued)

*Primary Examiner*—Anne Marie S Wehbe
(74) *Attorney, Agent, or Firm*—Wiley Rein LLP

(57) ABSTRACT

A medicinal combination of one or more nucleic acids that at least partially inhibit oncogenic cell signalling pathways, and a therapeutic anticancer agent, for use simultaneous, separate or over a period of time to treat hyperproliferative diseases.

5 Claims, 3 Drawing Sheets

OTHER PUBLICATIONS

Mastropaolo, Donald, et al., Crystal and Molecular Structure of Paclitaxel (taxol), Proc. Natl. Acad. Sci, USA, vol. 92, pp. 6920-6924, Jul. 1995.

Hellin, Anne-Cecile, et al., Roles of Nuclear Factor-kB, p53, and p21/WAF1 in Daunomycin-Induced Cell Cycle Arrest and Apoptosis, The Journal of Pharmacology and Experimental Therapeutics, vol. 295, No. 3, pp. 870-878 (2000).

Hainaut, Pierre, et al., "25 Years of p53 Research", (2005) (Foreward).

Ogawa, et al., "Experimental Cancer, Novel combination therapy for human colon cancer with adenovirus-mediated wild-type p53 gene transfer and DNA-damaging chemotherapeutic agent.", International Journal of Cancer, vol. 73, No. 3, pp. 367-370, Dec. 6, 1998 (Abstract).

National Cancer Institute Drug Dictionary, Definition of Docetaxel (Feb. 4, 2009).

National Cancer Institute Drug Dictionary, Definition of Paclitaxel (Feb. 4, 2009).

Disputes Involving Paclitaxel, a cancer drug sold under different brand name including Taxol (Feb. 4, 2009).

FDA Oncology Summary of Docetaxel (Feb. 4, 2009).

* cited by examiner

COMBINED THERAPEUTICAL TREATMENT OF HYPERPROLIFERATIVE DISEASES

RELATED APPLICATION INFORMATION

This application is a continuation of Ser. No. 09/816,144, filed Mar. 26, 2001, now abandoned, which is a continuation of Ser. No. 08/875,222, filed Jul. 17, 1997, now U.S. Pat. No. 6,262,032, which claims priority to PCT/FR96/00056, filed Jan. 12, 1996, and French application FR95/00436.

The present invention relates to the field of the therapy of hyperproliferative pathologies. It relates more especially to a new method of treatment of hyperproliferative pathologies based on the combined use of two types of therapeutic agents.

More specifically, the present invention relates to a new method of treatment of hyperproliferative pathologies based on the combined use of genes that block oncogenic cell signalling pathways and chemotherapeutic and or radiotherapeutic agents. The combined treatments according to the present invention have especially effective effects for the destruction of hyperproliferating cells, at relatively low doses. The present invention thus provides an especially effective new method of treatment of hyperproliferative pathologies (cancer, restenosis and the like) with limited side-effects.

In spite of the very substantial progress made in this field, the methods currently available for the treatment of cancer still have limited efficacy. Radiotherapy and chemotherapy admittedly have a very favourable impact on the development of cancers. However, an acute problem in the treatment of cancer is the insensitivity of certain primary tumours and/or the appearance of tumour cells which are resistant, after a first cycle of effective treatments, both to radio- and to chemo-therapy.

Numerous studies have attempted to elucidate the molecular mechanisms which may be the source of these events. Generally speaking, the investigations have been directed towards the manner in which chemotherapeutic agents entered the cells and the manner in which they reacted with their cell targets (Chin et al., Adv. Cancer Res. 60 (1993) 157-180; Chabner and Meyers in Cancer/Principles and practices of Oncology, De Vita et al. Eds., J.B. Lippencott Co. pp. 349-395, 1989). For example, high levels of expression of the mdr1 gene can limit the intracellular concentration of various chemotherapeutic agents and might contribute to the expression of the multiple drug resistance (Chin et al., see above).

A more complete elucidation of the mechanisms of resistance to chemotherapy and to radiotherapy involves a better knowledge of the processes of cell death induced by these agents. Since ionizing radiation and many anticancer agents induce damage in the DNA, the effect of these therapeutic agents has been attributed to their genotoxic power. However, the cell damage caused by these agents does not enable their therapeutic activity to be explained completely (Chabner and Meyers, see above). In the last few years, the exploration and understanding of the mechanisms of programmed death or apoptosis have enabled the mechanisms by which tumour cells acquire or lose their sensitivity to cytotoxic agents to be reconsidered. Numerous toxic stimuli induce apoptosis, even at doses which are insufficient to induce metabolic dysfunctions. The capacity to induce an apoptotic response in tumour cells might determine the efficacy of the treatment.

The applicant has now developed a new method of treatment which is especially effective for the destruction of hyperproliferative cells. As mentioned above, the method of treatment according to the invention is based essentially on the combined use of two types of therapeutic agents: genes that block oncogenic cell signalling pathways and chemotherapeutic and/or radiotherapeutic agents. The present invention is, in effect, the outcome of the demonstration of an especially large synergistic effect associated with the combined use of these two types of agents.

A first subject of the present invention hence relates to a medicinal combination of one or more nucleic acids that at least partially inhibit oncogenic cell signalling pathways and an anticancer therapeutic agent, for use simultaneously, separately or spread over time for the treatment of hyperproliferative pathologies.

As mentioned above, the invention is based essentially on the demonstration of a synergistic effect between the product of certain genes and anticancer therapeutic agents. This combined use produces more powerful effects at lower doses of agents. This invention thus affords an especially advantageous means for the treatment of hyperproliferative pathologies.

As mentioned later, depending on the gene and the chemo- or radiotherapeutic agent which are chosen, the two components of the combined treatment of the present invention may be used simultaneously, separately or spread over time. In the case of a simultaneous use, both agents are incubated with the cells or administered to the patient simultaneously. According to this embodiment of the present invention, the two agents may be packaged separately and then mixed at the time of use before being administered together. More commonly, they are administered simultaneously but separately. In particular, the administration see of the two agents can be different. In another embodiment, the two agents are administered spaced over time.

The nucleic acid used in the context of the present invention can be a deoxyribonucleic acid (DNA) or a ribonucleic acid (RNA). Among DNAs, possible alternatives include a complementary DNA (cDNA), a genomic DNA (gDNA), a hybrid sequence or a synthetic or semi-synthetic sequence. A further possibility is a nucleic acid modified chemically, for example, for the purpose of increasing its resistance to nucleases, its cell penetration or cell targeting, its therapeutic efficacy, and the like. These nucleic acids can be of human, animal, plant, bacterial, viral, synthetic and the like, origin. They may be obtained by any technique known to a person skilled in the art, and in particular by screening of libraries, by chemical synthesis or alternatively by mixed methods including the chemical or enzymatic modification of sequences obtained by screening of libraries. As mentioned later, they can, moreover, be incorporated in vectors such as plasmid, viral or chemical vectors.

As mentioned above, the nucleic acid according to the present invention is a nucleic acid capable of at least partially inhibiting oncogenic cell signalling pathways. These nucleic acids are designated hereinafter by the term "oncogene intracellular neutralization elements" or OINE. The signalling pathways leading to cell transformation are manifold. Cell proliferation involves a multitude of factors, such as membrane receptors (G proteins), oncogenes, enzymes (protein kinases, farnesyl transferases, phospholipases, and the like), nucleosides (ATP, AMP, GDP, GTP, and the like), activating factors [guanosine exchange factors (GRF, GAP, RAF, and the like), transcription factors, and the like], Disturbances, for example in the structure, activity, conformation, and the like, of these different factors have been associated with phenomena of deregulation of cell proliferation. Thus, 90% of adenocarcinomas of the pancreas possess a Ki-ras oncogene mutated on the twelfth codon (Almoguera et al., Cell 53 (1988) 549). Similarly, the presence of a mutated ras gene has been demonstrated in adenocarcinomas of the colon and thyroid cancers (50%), or in carcinomas of the lung and myeloid leukaemias (30%, Bos, J. L. Cancer Res. 49 (1989) 4682). Many other oncogenes have now been identified (myc, fos, jun, ras, myb, erb, and the like), mutated forms of which appear to be responsible for a disturbance of cell proliferation. Similarly, mutated forms of p53 are observed in many cancers, such as, in particular, colorectal cancer, breast cancer, lung cancer, stomach cancer, cancer of the oesophagus, B-cell lymphomas, ovarian cancer, bladder cancer, and the like. The nucleic acids used in the context of the invention are nucleic acids capable of interfering with one of these factors involved in cell proliferation, and of at least partially inhibiting its activity. The factors towards which the nucleic acids of the invention are preferentially directed are those which appear preferentially or specifically during disturbances of cell proliferation (activated oncogenes, mutant of tumour suppressor, and the like).

Nucleic acids used in the context of the invention can be of different types. Preferential possibilities are:
   antisense nucleic acids,
   oligoribonucleotides capable of binding oncogenic target proteins directly in order to neutralize them (ligand RNA),
   nucleic acids coding for proteins having dominant negative character, capable of oligomerizing and thereby producing an inactive complex,
   nucleic acids coding for intracellular antibodies (for example single-chain variable fragments originating from an antibody) directed against an oncogenic protein (ScFv).
   tumour suppressor genes.

Figure 1:
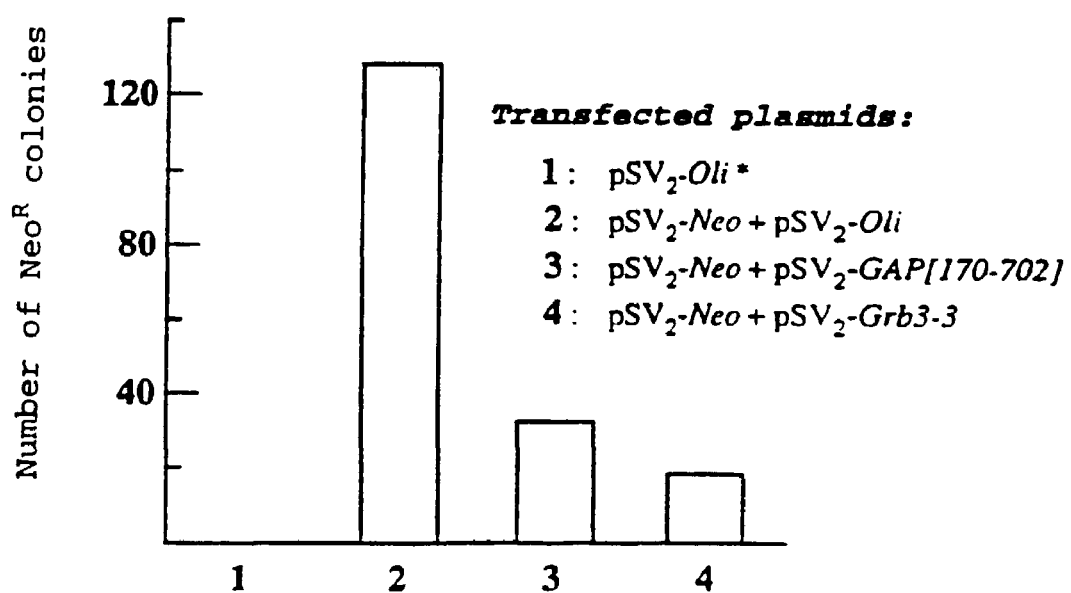
FIG. 1 depicts the results of an experiment representing the number of Neo resistant colonies under different transfection conditions.

According to a first preferred embodiment of the present invention, the nucleic acid is a DNA or an RNA coding for a polypeptide or protein that at least partially inhibits oncogenic cell signalling pathways. More especially, the polypeptide or protein are chosen from dominant negatives, ScFvs and tumour suppressors.

Still more preferably, the dominant negative is a constituent of the N-terminal region of the GAP protein, of the Gbr3-3 protein or of the mutants of Ets proteins. As regards ScFv, this is preferably an ScFv directed against a mutated ras protein or against the GAP factor. The tumour suppressor protein is advantageously p53, Rb, waf1, p21, DCC or MTS.

According to another preferred embodiment of the present invention, the nucleic acid is a DNA coding for an RNA that at least partially inhibits oncogenic cell signalling pathways. More especially, the RNA is an RNA complementary to a target nucleic acid and capable of blocking its transcription and/or its translation (antisense RNA); a ribozyme or a ligand RNA. A preferred example is an anti-Kiras antisense RNA.

Still according to a preferred embodiment of the present invention, the nucleic acid is an antisense oligonucleotide, where appropriate chemically modified. Possible oligonucleotides are ones whose phosphodiester skeleton has been chemically modified, such as, for example, the oligonucleotide phosphonates, phosphotriesters, phosphoramidates and phosphorothioates which are described, for example, in Patent Application WO94/08003. Other possibilities are alpha oligonucleotides or oligonucleotides conjugated to agents such as acrylating compounds.

In an especially preferred embodiment of the present invention, the nucleic acid is incorporated in a vector. The vector used can be of chemical origin (liposome, nanoparticle, peptide complex, cationic lipids, and the like), viral origin (retrovirus, adenovirus, herpesvirus, AAV, vaccinia virus, and the like) or plasmid origin. The nucleic acid used in the present invention may be formulated with a view to topical, oral, parenteral, intranasal, intravenous, intramuscular, subcutaneous, intraocular, transdermal, and the like, administration. Preferably, the nucleic acid is used in an injectable form. It may hence be mixed with any vehicle which is pharmaceutically acceptable for an injectable formulation, in particular for direct injection at the site to be treated. Possible formulations are, in particular, sterile isotonic solutions, or dry, in particular lyophilized, compositions which, on adding physiological saline or sterilized water as appropriate, enable injectable solutions to be made up. Direct injection of the nucleic acid into the patient's tumour is advantageous, since it enables the therapeutic effect to be concentrated in the affected tissues. The doses of nucleic acid used can be adapted in accordance with various parameters, and in particular in accordance with the gene, the vector, the method of administration used, the pathology in question or the desired treatment period.

The anticancer therapeutic agent used for carrying out the present invention can be any agent currently used by a person skilled in the art in chemotherapy or radiotherapy. It can, in particular, be cisplatin, taxoid, etoposide, TNF, adriamycin, camptothecin, a mitotic spindle poison (vinca alkaloids, navellein, and the like), X-rays, UV, and the like. Especially advantageous results have been obtained using a taxoid as chemotherapeutic agent. The anticancer chemotherapeutic agent is administered by the traditional routes. Generally, it is administered parenterally.

As mentioned above, the two agents may be used simultaneously, separately or spread over time. In an especially preferred embodiment of the invention, the nucleic acid is administered first and then, when the nucleic acid can be expressed by the cells or some cells, the anticancer therapeutic agent is administered.

An especially preferred embodiment of the present invention relates to a medicinal combination of one or more tumour suppressor genes and a taxoid, for use simultaneously, separately or spread over time for the treatment of hyperproliferative pathologies. Still more preferably, the suppressor gene codes for the wild-type form of the p53 protein or for the waf1 (p21) protein.

The present invention thus provides a method which is especially effective for the destruction of hyperproliferative cells. It may be used in vitro or ex vivo, by incubating the cells simultaneously or spread over time in the presence of the nucleic acid or acids and the chemotherapeutic agents. In this connection, the subject of the invention is also a method of destruction of hyperproliferative cells, comprising the bringing of the said cells or of a portion of them into contact with a nucleic acid and a chemotherapeutic agent as are defined above.

The present invention is advantageously used in vivo for the destruction of hyperproliferating (i.e. abnormally proliferating) cells. It is thus applicable to the destruction of tumour cells or of smooth muscle cells of the vascular wall (restenosis). It is most especially suitable for the treatment of cancers in which an activated oncogene is involved. As an example, there may be mentioned adenocarcinoma of the colon, thyroid cancer, carcinoma of the lung, myeloid leukaemias, colorectal cancer, breast cancer, lung cancer, stomach cancer, cancer of the oesophagus, B-cell lymphomas, ovarian cancer, bladder cancer, gliobastomas, and the like.

Use of Antisense Nucleic Acids

Regulation of the expression of target genes by means of antisense nucleic acids constitutes a therapeutic approach undergoing increasing development. This approach is based on the capacity of nucleic acids to hybridize specifically with complementary regions of another nucleic acid, and thereby to inhibit specifically the expression of particular genes. This inhibition can take place either at translational level or at transcriptional level.

Antisense nucleic acids are nucleic acid sequences capable of hybridizing selectively with target cell messenger RNAs to inhibit their translation to protein. These nucleic acids form locally, with the target mRNA, RNA/mRNA or even DNA/mRNA type double-stranded regions by classical Watson-Crick type interaction. Possible examples are small synthetic oligonucleotides complementary to cellular mRNAs and which are introduced into the target cells. Such oligonucleotides have, for example, been described in Patent No. EP 92 574. Other possible sequences are DNA sequences whose expression in the target cell generates RNAs complementary to cellular mRNAs. Such sequences have, for example, been described in Patent No. EP 140 308.

More recently, a new type of nucleic acid capable of regulating the expression of target genes has been demonstrated. These nucleic acids do not hybridize with cellular mRNAs, but directly with the double-stranded genomic DNA. This new approach is based on the demonstration that some nucleic acids are capable of interacting specifically in the major groove of the DNA double helix to form triple helices locally, leading to an inhibition of the transcription of target genes. These nucleic acids selectively recognize the DNA double helix at oligopurine.oligopyrimidine sequences, that is to say at regions possessing an oligopurine sequence on one strand and an oligopyrimidine sequence on the complementary strand, and form a triple helix locally thereat. The bases of the third strand (the oligonucleotide) form hydrogen bonds (Hoogsteen or reverse Hoogsteen bonds) with the purines of the Watson-Crick base pairs. Such nucleic acids have, in particular, been described by Helene in Anti-Cancer drug design 6 (1991) 569.

The antisense nucleic acids according to the present invention can be DNA sequences coding for antisense RNAs or for ribozymes. The antisense RNAs thereby produced can interact with a target mRNA or genomic DNA and form double or triple helices therewith. Other possible sequences are antisense (oligonucleotide) sequences, where appropriate chemically modified, capable of interacting directly with the target gene or RNA.

Preferably, the antisense sequences according to the invention are directed against activated oncogenes or specific regions of activated oncogenes, especially the ras oncogene.

Use of Ligand RNAs

Ligand RNAs are small oligoribonucleotides which are very specific and have very high affinity for a given target, in particular protein target. The preparation and identification of such ligand RNAs has been described, in particular, in Application WO91/19813. According to a particular embodiment of the present invention, it is possible to combine a small RNA specific for the Ki-ras protein, expressed in the cells by means of a suitable viral or non-viral vector, with the chemotherapeutic or radiotherapeutic agents described.

Dominant Negatives

A dominant negative is a polypeptide antagonist of an oncogenic signalling pathway. This antagonism takes place when the polypeptide becomes positioned in contact with a key element of the oncogenic signalling and enters into competition with the polypeptide naturally used in the cell for this signalling. The polypeptide antagonist used is very frequently a mimic of the natural polypeptide but which lacks domains that enable the oncogenic signal to be propagated through it.

Among dominant negatives preferred for carrying out the present invention, there may be mentioned the nucleic acids coding for the NH2-terminal domain of the GAP protein, for the Grb3-3 protein or for mutated forms of the ETS proteins.

It has been demonstrated in Patent Application WO94/03597 that the overexpression of the NH2-terminal domain of the GAP-Ras protein could specifically block the tumorigenicity of cells transformed following the expression of a mutated ras gene. Example 1 of the present application now shows that an overexpression of the GAP(170-702) domain induces an apoptosis of human cells, so-called non-small cell carcinoma of the lung (H460). Example 2 shows, furthermore, that the apoptotic effect induced by the GAP (170-702) construction is very greatly increased by the addition of products such as cisplatin, camptothecin or taxotere to the culture medium of human tumour cells, at concentrations of these products which are without effect on cell viability.

Example 1 of the present application describes, moreover, the activity of the grb3-3 gene in H460 cells. The sequence and the presumed function of Grb3-3 have been described in Science 1994. Example 2 also shows that the apoptotic effect induced by the transfer of the Grb3-3 gene is very greatly increased by the addition of products such as cisplatin, camptothecin or taxotere to the culture medium of human tumour cells, at concentrations of these products which are without effect on cell viability.

These examples demonstrate clearly that different chemotherapeutic agents can be effectively combined with strategies for induction of apoptosis by means of gene transfer.

ScFvs

ScFvs are intracellularly active molecules having binding property comparable to that of an antibody. They are, more especially, molecules consisting of a peptide corresponding to the binding site of the light chain variable region of an antibody, linked via a peptide linker to a peptide corresponding to the binding site of the heavy chain variable region of an antibody. It has been shown by the applicant that such ScFvs could be produced in vivo by gene transfer (see Application WO94/29446).

More especially, this application shows that it is possible to neutralize oncogenic proteins by expressing ScFvs in different cell compartments. According to an embodiment of the present invention, a nucleic acid permitting the intracellular production of an ScFv which neutralizes the transforming power of the ras proteins is used in combination with a chemotherapeutic agent. Such a combination produces substantial synergistic effects (see Example 2).

Tumour Suppressors

Among the tumour suppressor genes which can be used in the context of the present invention, the p53, p21, Rb, rap1A, DDC, WAF and MTS genes may be mentioned more especially. More especially, the p53, Rb or Waf genes are used.

The p53 gene codes for a nuclear protein of 53 kDa. The form of this gene mutated by deletion and/or mutation is involved in the development of most human cancers (Baker et al., Science 244 (1989) 217). Its mutated forms are also capable of cooperating with the ras oncogenes to transform mouse fibroblasts. The wild-type gene coding for native p53 inhibits, on the other hand, the formation of foci of transformation in rodent fibroblasts transfected with various combinations of oncogenes. Recent data emphasize the fact that the p53 protein could itself be a transcription factor and could stimulate the expression of other tumour suppressor genes. Moreover, an effect of p53 on the proliferation of vascular smooth muscle cells has been demonstrated recently (Epstein et al., Science 151 (1994)).

The Rb gene determines the synthesis of a nuclear phosphoprotein of approximately 927 amino acids (Friend et al., Nature 323 (1986) 643) whose function is to repress cell division by making the cells enter a quiescent phase. Inactivated forms of the Rb gene have been implicated in various tumours, and in particular in retinoblastomas or in mesenchymal cancers such as osteosarcoma. Reintroduction of this gene into the tumour cells in which it was inactivated produces a return to the normal state and a loss of the tumorigenicity (Huang et al., Science 242 (1988) 1563). Recently, it has been demonstrated that the normal Rb protein, but not its mutated forms, represses the expression of the c-fos proto-oncogene, a gene essential for cell proliferation.

The WAF and MTS genes and their antitumour properties have been described in the literature (Cell 75 (1993) 817; Science 264 (1994) 436).

Example 3 demonstrates an effective type of combination between a taxol derivative and the p53 gene. Taxol induces apoptosis in various tumour cell lines in culture (Proceedings of the American Association for cancer Research Vol. 35, march 1994, Bhalla et al., p306, Seiter et al., p314, Saunders et al., p317). p53 triggers an apoptosis in various cell types. We have now been able to show that the combination of a taxol derivative and p53 induces an apoptosis of human tumour cells. Notably, particular clones of H460 cells which were resistant to the effect of p53 were cultured in the presence of increasing doses of taxotere. Example 3 demonstrates clearly that the cells die following the treatment with taxotere at concentrations which are completely ineffective on cells that do not express wild-type p53.

Waf 1 (wild-type p53 activated fragment Cell, 75, 817, 1993), or alternatively p21 (Nature, 366, 701, 1993), is induced by the overexpression of wild-type p53. Waf 1 appears in cells which have stopped in the G1 phase or in apoptosis following an overexpression of wild-type p53, but not in cells which have stopped in G1 or in apoptosis in a p53-independent manner (Cancer Res, 54, 1169, 1994). Waf 1 decreases the growth of tumour cells as effectively as wild-type p53. The combined use of a Waf 1 gene and taxol derivatives also induces a synergistic effect on the destruction of hyperproliferative cells.

Anticancer Therapeutic Agent

The anticancer therapeutic agents which can be used in the combined therapy according to the present invention can be chosen from all chemotherapeutic or radiotherapeutic agents known to a person skilled in the art. Possible agents are, in particular, cisplatin, taxoid, etoposide, TNF, adriamycin, camptothecin, a mitotic spindle poison, and the like. These various agents may be obtained from a commercial source.

Among these agents, the taxoids constitute a preferred embodiment. In this connection, the taxoids which can be used more especially in the context of the present invention are those which are represented by the general formula:

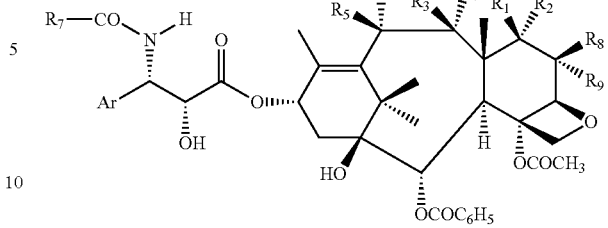

in which:

the symbols $R_1$ and $R_2$ each represent a hydrogen atom, or alternatively one of the radicals $R_1$ or $R_2$ represents a hydrogen atom and the other represents a hydroxyl, acyloxy or acylcarbonyloxy radical, or alternatively $R_2$ represents a hydrogen atom and $R_1$ forms a bond with the carbon atom of the methyl radical at the α-position, so as to form a cyclopropane ring, one of the symbols $R_3$ or $R_4$ represents a hydrogen atom, and the other represents a hydroxyl radical, or alternatively $R_3$ and $R_4$ together form a carbonyl radical, the symbols $R_5$ and $R_6$ each represent a hydrogen atom, or alternatively one of the symbols $R_5$ or $R_6$ represents a hydrogen atom and the other represents a hydroxyl, acyloxy, acylcarbonyloxy or alkoxymethylcarbonyloxy radical, or alternatively $R_5$ and $R_6$ together form a carbonyl radical, the symbols $R_8$ and $R_9$ each represent a hydrogen atom, or alternatively $R_1$ and $R_8$ together form a bond, the symbol $R_7$ represents an alkoxy, alkenyloxy or cycloalkyloxy radical or a phenyl radical, and Ar represents a phenyl radical optionally substituted with one or more identical or different atoms or radicals chosen from halogen atoms and alkyl, alkoxy, dialkylamino, acylamino, alkoxycarbonylamino or trifluoromethyl radicals, or a 5-membered aromatic heterocyclic radical containing one or more identical or different hetero atoms chosen from nitrogen, oxygen and sulphur atoms, on the understanding that the alkyl radicals and the alkyl portions of the other radicals contain 1 to 8 carbon atoms in an unbranched or branched chain and that the alkenyl radicals contain 2 to 8 carbon atoms.

More especially advantageous are the taxoids for which, $R_2$ representing a hydrogen atom, $R_1$ represents a hydrogen atom or a hydroxyl radical or alternatively $R_1$ forms a single bond with the carbon atom of the methyl radical at the α-position, $R_3$ and $R_4$ together form a carbonyl radical, $R_5$ represents a hydrogen atom and $R_6$ represents a hydrogen atom or a hydroxyl, acetyloxy or methoxyacetyloxy radical or alternatively $R_5$ and $R_6$ together form a carbonyl radical, and $R_7$ represents a t-butoxy radical or a phenyl radical.

The following products may be mentioned more especially:

4-acetoxy-2α-benzoyloxy-5β,20-epoxy-1β,7β,10β-trihydroxy-9-oxo-11-taxen-13α-yl (2R,3S)-3'-t-butoxycarbonylamino-3'-phenyl-2'-hydroxypropionate (docetaxel or Taxotère®)

4,10β-diacetoxy-2α-benzoyloxy-5β,20-epoxy-1β,7β-dihydroxy-9-oxo-11-taxen-13α-yl (2R,3S)-3'-benzoylamino-3'-phenyl-2'-hydroxypropionate (paclitaxel)

4-acetoxy-2α-benzoyloxy-5β,20-epoxy-1β,10β-dihydroxy-7β,10β-methylene-19-nor-9-oxo-11-taxen-13α-yl (2R, 3S)-3'-t-butoxycarbonylamino-3'-phenyl-2'-hydroxypropionate 4,10β-diacetoxy-2α-benzoyloxy-5β,20-epoxy-1β-hydroxy-7β,10β-methylene-19-nor-9-oxo-11-taxen-13α-yl (2R,3S)-3'-t-butoxycarbonylamino-3'-phenyl-2'-hydroxypropionate, 4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(2-fluorophenyl)-2'-hydroxypropionate 4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(4-chlorophenyl)-2'-hydroxypropionate 4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(4-methoxyphenyl)-2'-hydroxypropionate 4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(4-fluorophenyl)-2'-hydroxypropionate 4-acetoxy-2α-benzoyloxy-5β,20-epoxy-1β,7β,10β-trihydroxy-9-oxo-11-taxen-13α-yl (2R,3S)-3'-adamantyloxycarbonylamino-3'-phenyl-2'-hydroxypropionate 4-acetoxy-2α-benzoyloxy-5β,20-epoxy-1β,7β,10β-trihydroxy-9-oxo-11-taxen-13α-yl (2R,3S)-3'-tert-pentyloxycarbonylamino-3'-phenyl-2'-hydroxypropionate 4-acetoxy-2α-benzoyloxy-5β,20-epoxy-1β,7β,10β-trihydroxy-9-oxo-11-taxen-13α-yl (2R,3S)-3'-(1-methylcyclohexyl)oxycarbonylamino-3'-phenyl-2'-hydroxypropionate 4-acetoxy-2α-benzoyloxy-5β,20-epoxy-1β,7β,10β-trihydroxy-9-oxo-11-taxen-13α-yl (2R,3S)-3'-(1-methylcyclopropyl)oxycarbonylamino-3'-phenyl-2'-hydroxypropionate 4-acetoxy-2α-benzoyloxy-5β,20-epoxy-1β,7β,10β-trihydroxy-9-oxo-11-taxen-13α-yl (2R,3S)-3'-(1-methylcyclopentyl)oxycarbonylamino-3'-phenyl-2'-hydroxypropionate 4-acetoxy-2α-benzoyloxy-5β,20-epoxy-1β,7β,10β-trihydroxy-9-oxo-11-taxen-13α-yl (2R,3S)-3'-(1,1-dimethyl-2-propyn)yloxycarbonylamino-3'-phenyl-2'-hydroxypropionate 4-acetoxy-2α-benzoyloxy-5β,20-epoxy-1β,7β,9β,10β-tetrahydroxy-11-taxen-13α-yl (2R,3S)-3'-t-butoxycarbonylamino-3'-phenyl-2'-hydroxypropionate 4-acetoxy-2α-benzoyloxy-5β,20-epoxy-1β,7β-dihydroxy-9-oxo-11-taxen-13α-yl (2R,3S)-3'-t-butoxycarbonylamino-3'-phenyl-2'-hydroxypropionate 4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(2-thienyl)-2'-hydroxypropionate 4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(2-furyl)-2'-hydroxypropionate 4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(3-thienyl)-2'-hydroxypropionate 4-acetoxy-2α-benzoyloxy-5β,20-epoxy-1β,10β-dihydroxy-9-oxo-11-taxen-13α-yl (2R,3S)-3'-t-butoxycarbonylamino-3'-phenyl-2'-hydroxypropionate 4-acetoxy-2α-benzoyloxy-5β,20-epoxy-1β,7β-dihydroxy-9,10-dioxo-11-taxen-13α-yl (2R,3S)-3'-t-butoxycarbonylamino-3'-phenyl-2'-hydroxypropionate 4-acetoxy-2α-benzoyloxy-5β,20-epoxy-1β-hydroxy-9-oxo-11-taxen-13α-yl (2R,3S)-3'-t-butoxycarbonylamino-3'-phenyl-2'-hydroxypropionate These different compounds may be obtained according to the methods described in Applications WO94/13654 and WO92/09589, for example, which are incorporated in the present application by reference.

It is especially advantageous, for the purposes of the present invention, to use taxol, docetaxel or paclitaxel.

Vectors for Administration of the Nucleic Acid

The nucleic acid may be injected as it is at the site to be treated, or incubated directly with the cells to be destroyed or treated. It has, in effect, been reported that naked nucleic acids could enter cells without a special vector. Nevertheless, it is preferable in the context of the present invention to use an administration vector, enabling (i) the efficacy of cell penetration, (ii) targeting and (iii) extra- and intracellular stability to be improved.

Different types of vectors can be used. The vectors can be viral or non-viral.

Viral Vectors

The use of viral vectors is based on the natural properties of transfection of viruses. It is thus possible to use adenoviruses, herpesviruses, retroviruses and, more recently, adeno-associated viruses. These vectors prove especially efficacious from the standpoint of transfection.

As regards adenoviruses more especially, different serotypes, the structure and properties of which vary somewhat, have been characterized. Among these serotypes, it is preferable to use, in the context of the present invention, human adenoviruses type 2 or 5 (Ad 2 or Ad 5) or adenoviruses of animal origin (see Application WO94/26914). Among adenoviruses of animal origin which can be used in the context of the present invention, adenoviruses of canine, bovine, murine (for example: Mav1, Beard et al., Virology 75 (1990) 81), ovine, porcine, avian or alternatively simian (for example: SAV) origin may be mentioned. Preferably, the adenovirus of animal origin is a canine adenovirus, and more preferably a CAV2 adenovirus [strain Manhattan or A26/61 (ATCC VR-800), for example]. It is preferable to use adenoviruses of human or canine or mixed origin in the context of the invention.

Preferably, the defective adenoviruses of the invention comprise the ITRs, a sequence permitting encapsidation and the nucleic acid of interest. Still more preferably, in the genome of the adenoviruses of the invention, the E1 region at least is non-functional. The viral gene in question may be rendered non-functional by any technique known to a person skilled in the art, and in particular by total elimination, substitution, partial deletion or addition of one or more bases in the gene or genes in question. Such modifications may be obtained in vitro (on the isolated DNA) or in situ, for example by means of genetic engineering techniques, or alternatively by treatment by means of mutagenic agents. Other regions may also be modified (E2, E3, E4, L1-L5, and the like).

The defective recombinant adenoviruses according to the invention may be prepared by any technique known to a person skilled in the art (Levrero et al., Gene 101 (1991) 195, EP 185 573; Graham, EMBO J. 3 (1984) 2917). In particular, they may be prepared by homologous recombination between an adenovirus and a plasmid carrying, inter alia, the DNA sequence of interest. Homologous recombination takes place after cotransfection of the said adenovirus and said plasmid into a suitable cell line. The cell line used should preferably (i) be transformable by the said elements, and (ii) contain the sequences capable of complementing the portion of the genome of the defective adenovirus, preferably in integrated form in order to avoid risks of recombination. As an example of a line, there may be mentioned the human embryonic kidney line 293 (Graham et al., J. Gen. Virol. 36 (1977) 59) which contains, in particular, integrated in its genome, the left-hand portion of the genome of an Ad5 adenovirus (12%).

Strategies of construction of vectors derived from adenoviruses have also been described in Applications Nos. WO 94/26914 and FR 93 08596.

Thereafter, the adenoviruses which have multiplied are recovered and purified according to standard techniques of molecular biology, as illustrated in the examples.

Adeno-associated viruses (AAV) are, for their part, relatively small-sized DNA viruses which integrate stably and in a site-specific manner in the genome of the cells they infect. They are capable of infecting a broad range of cells without inducing an effect on cell growth, morphology or differentiation. Moreover, they do not appear to be implicated in pathologies in man. The AAV genome has been cloned, sequenced and characterized. It comprises approximately 4700 bases, and contains at each end an inverted repeat region (ITR) of approximately 145 bases, serving as origin of replication for the virus. The remainder of the genome is divided into 2 essential regions carrying the encapsidation functions: the left-hand portion of the genome, which contains the rep gene involved in the viral replication and expression of the viral genes; and the right-hand portion of the genome, which contains the cap gene coding for the capsid proteins of the virus.

The use of vectors derived from AAVs for the transfer of genes in vitro and in vivo has been described in the literature (see, in particular, WO 91/18088; WO 93/09239; U.S. Pat. No. 4,797,368, U.S. Pat. No. 5,139,941, EP 488 528). These applications describe different constructions derived from AAVs, in which the rep and/or cap genes are deleted and replaced by a gene of interest, and their use for transferring the said gene of interest in vitro (to cells in culture) or in vivo (directly into a body). The defective recombinant AAVs according to the invention may be prepared by cotransfection, into a cell line infected with a human helper virus (for example an adenovirus), of a plasmid containing the nucleic acid sequence of interest flanked by two inverted repeat regions (ITR) of AAV, and a plasmid carrying the encapsidation genes (rep and cap genes) of AAV. The recombinant AAVs produced are then purified by standard techniques.

Regarding herpesviruses and retroviruses, the construction of recombinant vectors has been amply described in the literature: see, in particular, Breakfield et al., New Biologist 3 (1991) 203; EP 453242, EP178220, Bernstein et al. Genet. Eng. 7 (1985) 235; McCormick, BioTechnology 3 (1985) 689, and the like. In particular, retroviruses are integrative viruses which selectively infect dividing cells. They hence constitute vectors of interest for cancer applications. The retrovirus genome essentially comprises two LTRs, an encapsidation sequence and three coding regions (gag, pol and env). In the recombinant vectors derived from retroviruses, the gag, pol and env genes are generally deleted wholly or partially, and replaced by a heterologous nucleic acid sequence of interest. These vectors may be produced from different types of retrovirus such as, in particular, MoMuLV (Moloney murine leukaemia virus; also designated MoMLV), MSV (Moloney murine sarcoma virus), HaSV (Harvey sarcoma virus), SNV (spleen necrosis virus), RSV (Rous sarcoma virus) or alternatively Friend virus.

To construct recombinant retroviruses containing a sequence of interest, a plasmid containing, in particular, the LTRs, the encapsidation sequence and the said sequence of interest is generally constructed, and then used to transfect a so-called encapsidation cell line capable of providing in trans the retroviral functions which are deficient in the plasmid. Generally, the encapsidation lines are hence capable of expressing the gag, pol and env genes. Such encapsidation lines have been described in the prior art, and in particular the line PA317 (U.S. Pat. No. 4,861,719), the line PsiCRIP (WO90/02806) and the line GP+envAm-12 (WO89/07150). Moreover, the recombinant retroviruses can contain modifications in the LTRs to eliminate transcriptional activity, as well as extended encapsidation sequences containing a portion of the gag gene (Bender et al., J. Virol. 61 (1987) 1639). The recombinant retroviruses produced are then purified by standard techniques.

To implement the present invention, it is most especially advantageous to use a defective recombinant adenovirus or retrovirus. These vectors possess, in effect, especially advantageous properties for the transfer of genes into tumour cells.

Non-Viral Vectors

The vector according to the invention can also be a non-viral agent capable of promoting the transfer of nucleic acids to eukaryotic cells and their expression therein. Chemical or biochemical vectors represent an advantageous alternative to natural viruses, especially for reasons of convenience and safety and also on account of the absence of theoretical limit regarding the size of the DNA to be transfected.

These synthetic vectors have two main functions, to compact the nucleic acid which is to be transfected and to promote its binding to the cell as well as its passage through the plasma membrane and, where appropriate, both nuclear membranes. To compensate for the polyanionic nature of nucleic acids, non-viral vectors all possess polycationic charges.

Among the synthetic vectors developed, cationic polymers of the polylysine, (LKLK)n, (LKKL)n, polyethylenimine and DEAE-dextran type, or alternatively cationic lipids or lipofectants are the most advantageous. They possess the property of condensing DNA and of promoting its association with the cell membrane. Among the latter compounds, there may be mentioned lipopolyamines (lipofectamine, transfectam, and the like) and various cationic or neutral lipids (DOTMA, DOGS, DOPE, and the like). More recently, the concept of receptor-mediated, targeted transfection has been developed, which turns to good account the principle of condensing DNA by means of the cationic polymer while directing the binding of the complex to the membrane as a result of a chemical coupling between the cationic polymer and the ligand for a membrane receptor present at the surface of the cell type which it is desired to graft. Targeting of the transferrin or insulin receptor or of the asialoglycoprotein receptor of hepatocytes has thus been described.

Administration Protocol

A preferred administration protocol according to the invention comprises first the nucleic acid and then the therapeutic agent. In a preferential use, administration of the transgene is repeated in order to obtain a maximum expression in a maximum number of dividing cells (for example 5 days in succession), and the chemotherapeutic treatment is then administered. Advantageously, the nucleic acid or acids are administered in contact with the lesion, either by direct intratumoral injection into multiple sites of the lesion, or in contact with the atheromatous lesion by means of a cushion suited to this type of operation. The chemotherapeutic agent is administered according to the clinical protocols in force.

EXAMPLES

Example 1

H460 cells, cultured in RPMI 1640 medium containing 10% of fetal calf serum, are transfected with cDNAs coding for the GAP[170-702] domain or for the Grb3-3 protein in combination with a gene conferring resistance to geneticin (Neo) on the positively transfected cells. These cDNAs, placed in plasmids and whose expression is under the control of viral promoters (pSV$_2$-GAP[170-702], pSV$_2$-Grb3-3 and pSV$_2$-Neo), are introduced into the H460 cells using lipofectAMINE as transfecting agent. The H460/Neo$^R$ cells (resistant to the presence of 400 µg/ml of geneticin in the culture medium) are selected and quantified 15-20 days after transfection. The results of an experiment which is representative of quantification of the number of Neo$^R$ colonies under the different transfection conditions are summarized in FIG. 1 (pSV$_2$-Oli: control plasmid not possessing any cDNA of interest and thus permitting monitoring of the efficacy of the selection by geneticin).

Example 2

Figure 2:
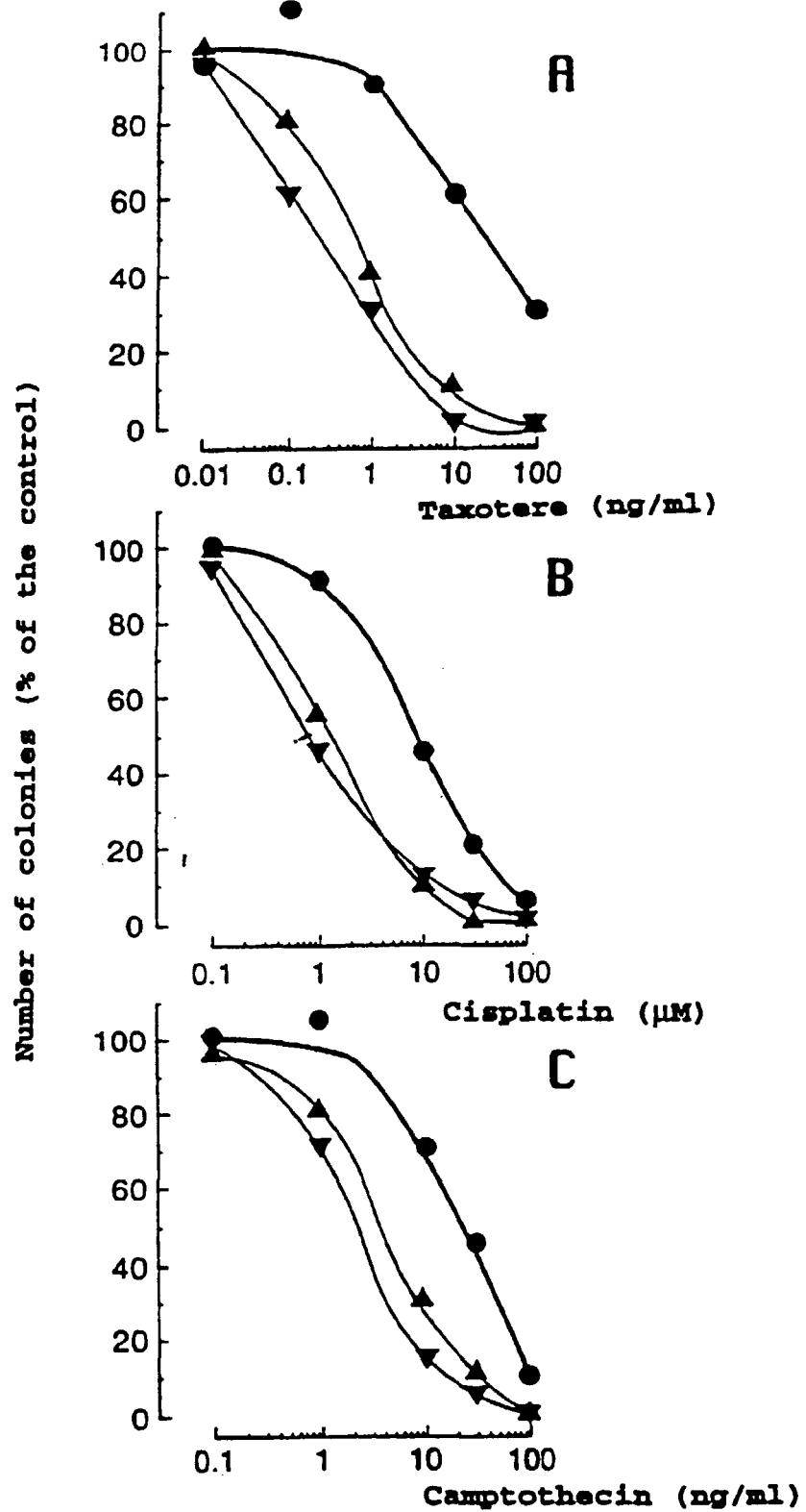
FIG. 2 A, B, C depicts the results of an experiment representing the number of colonies present with the different treatments noted.

H460 cells transfected as described in Example 1 are subjected during selection by geneticin to a treatment for several days at different concentrations of taxotere, of cisplatin or of camptothecin. The H460/Neo$^R$ cells and which are resistant to the chemotherapeutic agents are quantified as described in Example 1. The sensitivity to taxotere (A), to cisplatin (B) or to camptothecin (C) of the H460 cells transfected with pSV$_2$-Neo (●), pSV$_2$-Neo+pSV$_2$-GAP[170-702] (▲) or pSV$_2$-Neo+pSV$_2$-Grb3-3 (▼) is depicted relative to cells transfected identically but in the absence of treatment with the chemotherapeutic agents. The results of an experiment which is representative of quantification of the number of colony after the different treatments mentioned are summarized in FIG. 2.

Example 3

Figure 3:
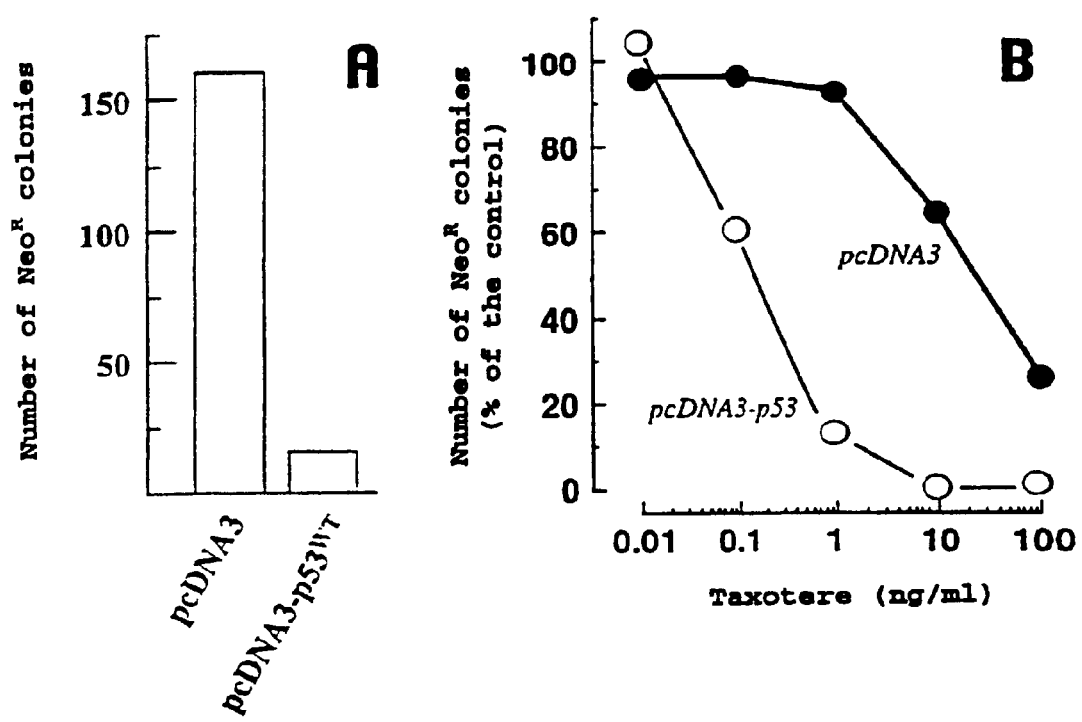
FIG. 3 summarizes the results of a representative experiment where the number of colonies obtained after transfection with pcDNA3 or pcDNA3-p53$^{wt}$ plasmids (A) and the sensitivity of isolated clones to taxotere treatment (B).

H460 cells are transfected with cDNA coding for the wild-type p53 protein (p53$^{WT}$) placed in the plasmid pcDNA3 under the control of the CMV promoter. Plasmid pcDNA3 also contains the Neo gene placed under the control of the SV40 promoter. Cells transfected with pcDNA3 or pcDNA3-p53$^{WT}$ are selected and isolated as described in Example 1. In the cells transfected with pcDNA3-p53$^{WT}$ and which are resistant to geneticin, the presence of p53 is verified by western blotting using specific antibodies. FIG. 3 summarizes the results of a representative experiment in which are depicted, on the one hand the number of colonies obtained after pcDNA3 or pcDNA3-p53$^{WT}$ transfection (A), and on the other hand the sensitivity of the clones isolated to a treatment with taxotere (B).

The invention claimed is:

1. A method of treatment of hyperproliferative tumor cell pathologies comprising intratumorally administering a combination of (a) a wild type-form of p53 nucleic acid that inhibits an oncogenic cell signaling pathway, and (b) a taxoid; wherein the nucleic acid and the taxoid are used simultaneously, separately or spread over time, and the nucleic acid is administered in an adenoviral vector.

2. The method according to claim 1, wherein the taxoid is selected from the group consisting of taxol, docetaxel, and paclitaxel.

3. The method according to claim 1, wherein the nucleic acid and the taxoid are used simultaneously.

4. The method according to claim 1, wherein the nucleic acid is administered before the taxoid.

5. A method for treatment of hyperproliferative tumor cell pathologies comprising administering a combination of a tumor suppressor gene in an adenoviral vector by intratumoral administration and a taxoid simultaneously, separately, or spread over time, wherein the tumor suppressor gene codes for the wild-type form of p53 protein.

* * * * *